United States Patent [19]
Menzel et al.

[11] Patent Number: 6,007,796
[45] Date of Patent: Dec. 28, 1999

[54] COSMETIC SELF-TANNING AGENT HAVING A SUNSCREEN EFFECT

[75] Inventors: Anette Menzel, Morris Plains; Ralph Macchio, Flanders; Klaus Stanzl, White Plains, all of N.J.; Leonhard Zastrow, Monaco, Monaco

[73] Assignee: Lancaster Group GmbH, Mainz, Germany

[21] Appl. No.: 09/091,974

[22] PCT Filed: Jan. 17, 1997

[86] PCT No.: PCT/DE97/00119

§ 371 Date: Jun. 26, 1998

§ 102(e) Date: Jun. 26, 1998

[87] PCT Pub. No.: WO97/25970

PCT Pub. Date: Jul. 24, 1997

[30] Foreign Application Priority Data

Jan. 17, 1996 [DE] Germany .......................... 196 03 018

[51] Int. Cl.⁶ ................ A61K 7/42; A61K 7/44; A61K 7/00
[52] U.S. Cl. ............... 424/59; 424/60; 424/400; 424/401
[58] Field of Search ................ 424/89, 60, 400, 424/401

[56] References Cited

U.S. PATENT DOCUMENTS 4,217,344  8/1980  Vanlerberghe et al. .................. 424/60

FOREIGN PATENT DOCUMENTS

| 0627214A1 | 5/1994 | European Pat. Off. . |
| WO/92/17159 | 10/1992 | WIPO . |
| WO/92/19214 | 11/1992 | WIPO . |
| WO/94/02176 | 2/1994 | WIPO . |
| WO/94/23693 | 10/1994 | WIPO . |

*Primary Examiner*—Shelley A. Dodson
*Attorney, Agent, or Firm*—Collard & Roe, P.C.

[57] ABSTRACT

The invention concerns a cosmetic self-tanning agent based on dihyroxyacetone and having a sunscreen effect. The object of the invention is to prepare an agent in which the self-tanning effect occurs shortly after application and over a long period of time, and in which a plurality of color shades can be obtained without additional color components. According to the invention, the agent contains: specific portions of one or a plurality of UV filters selected from the group comprising octylsalicylate, octylmethoxycinnamate and benzophenone-3 and their mixtures; dihydroxyacetone (DHA) in a liposomal carrier system and additionally unencapsulated DHA; an antioxidant selected from the group comprising tocopherol, ascorbic acid, calendula extract and a mixture thereof; a moisturizer selected from the group comprising aloe vera, phospholipids, phospholipid mixtures, sodium hyaluronate, glycerol and mixtures thereof; and cosmetic carrier substances and additives.

9 Claims, No Drawings

COSMETIC SELF-TANNING AGENT HAVING A SUNSCREEN EFFECT

This application is a 371 of PCT/DE97/00119 filed Jan. 17, 1997.

The invention relates to a cosmetic self-tanning agent based on dihydroxyacetone with a sunscreen effect, making it possible to obtain different color shades on the skin in addition to the sunscreen effect.

It has been known for many years that dihydroxyacetone (DHA) can be used as a tanning agent for human skin. DHA is formulated with various additives to compensate for the disadvantages normally inherent in this product. DHA is known to produce a somewhat unnatural orange color on the skin, and it is also highly reactive with other ingredients of a mixture, decomposes rapidly and has an odor that is unacceptable for cosmetics. In addition, the skin coloring procedure usually takes too long (several hours) and then fades too rapidly (after a few hours to a few days).

A combination of a tanning agent based on DHA and a sunscreen is known from International Patent WO 94/23693, which concerns an O/W emulsion containing 0.1% to 20% DHA, 0.1% to 30% of a sunscreen, selected from a large group of such preparations, and 0.1% to 10% of a cross-linked cationic polymer and 0,1–10% of a cationic emulsifier.

European Patent A 627,214 discloses a self-tanning DHA formulation which also contains a pigment such as an eosin derivative that adheres to the skin.

U.S. Pat. No. 4,217,344 describes a sunscreen and tanning agent based on DHA which also contains tartaric aldehyde and a special dispersion of microspheres.

The object of the present invention is to provide a cosmetic self-tanning agent that is effective in several regards. With the help of a combination of active ingredients, an average sunscreen effect and a self-tanning effect are to be achieved at the same time, with the self-tanning effect being manifested after a short time and lasting a long time, and several different color shades for different skin types can be achieved without additional coloring components due to a difference in formulation of the active ingredients.

This object is achieved according to this invention with a cosmetic self-tanning agent with a sunscreen effect based on dihydroxyacetone, which is characterized in that it contains the following components, based on the total weight of the emulsion:

(a) one or more UV filters selected from the group consisting of octyl salicylate, octyl methoxycinnamate and benzophenone-3 and mixtures thereof in an amount of 2 to 7.5 percent by weight of the individual components and an amount of 7 to 18.5 percent by weight of the mixture of individual components;

(b) dihydroxyacetone (DHA) in a liposomal transport system consisting of DHA and phospholipids with a DHA content of 0.5 to 5 percent by weight, where the amount of liposomal solution is in the range of 1.5 to 25 percent by weight, plus also unencapsulated DHA in an amount of 1 to 4 percent by weight;

(c) an antioxidant selected from the group consisting of tocopherol, ascorbic acid, calendula extract and a mixture thereof in an amount of 0.01 to 5.0 percent by weight;

(d) a moisturizer selected from the group consisting of aloe vera, phospholipids, sodium hyaluronate, glycerol and mixtures thereof, with the moisturizer(s) in an amount of 0.1 to 16 percent by weight; and conventional cosmetic vehicles and additives. The amounts given are all based on the weight of the total preparation.

The total amount of the UV filters (a) is preferably in the range of 10 to 16 percent by weight. These UV filters (a) are preferably in a mixture of octyl salicylate, octyl methoxycinnamate and benzophenone-3, where the ratio of components to one another is in the range of 1.0–2.0:0.8–2.5:0.8–2.0. An especially preferred ratio is 1:2:1.

In addition, however, melanin in soluble form (up to approx. 0.05 percent by weight) and butylmethoxydibenzoylmethane (up to 5 percent by weight) may also be used as UV filters.

Other preferred ranges of the above components are 0.8 to 1.8 percent by weight for DHA (b), where the amount of the liposomal solution is in the range of 1.5 to 10.0 percent by weight. The amount of antioxidant (c) is preferably in the range of 0.01 to 0.5 percent by weight, and the amount of moisturizer (d) is preferably in the range of 0.7 to 5 percent by weight.

In a preferred embodiment, aloe vera and phospholipids are present concurrently as moisturizers, and then glycerol or sodium hyaluronate is optionally also present.

According to this invention, a self-tanning effect in natural appearing skin colors is achieved on different types of skin. The tanning of the skin begins after approximately 30 to 40 minutes and lasts for up to 14 days; in addition to the sunscreen effect, there is also a definite moisturizing effect on the skin. The formulation penetrates easily into the upper layers of skin as far as the stratum corneum, resulting in a short application time.

The sunscreen factor achieved is SPF 6–8.

A special advantage of the present invention is that at least three different basic color shades can be achieved with the active ingredients of the groups listed as (a) through (d) above merely by using different formulations of the preparation.

The three basic color shades are:

1. A light (or glowing) golden color (light golden glow), i.e., in the range of a yellowish brown tone;

2. A medium to dark golden bronze color (medium/dark golden bronze), i.e., in the range of a darker yellowish brown tone;

3. A medium to dark rosy bronze color (medium/dark rosy bronze), i.e., in the range of a more reddish brown tone.

All the cosmetic formulations of the three basic shades or colors are hypoallergenic and are not irritating to the skin, which is a special advantage in comparison with other products.

To achieve a light golden color, the preparation contains the following ingredients:

(a) the mixture of octyl salicylate, octyl methoxycinnamate and benzophenone-3 in a ratio of 1.0–2.0:0.8–2.5:0.8–2.0, where the amount of each individual UV filter is in the range of 3 to 7.5 percent by weight;

(b) DHA in a liposomal carrier system with a DHA content of 0.5 to 1.0 percent by weight, plus also unencapsulated DHA in an amount of 1.4 to 2.6 percent by weight;

(c) an antioxidant mixture in an amount of 0.15 to 0.25 percent by weight;

(d) a moisturizer mixture with glycerol in an amount of 2.5 to 4 percent by weight;

plus other cosmetic vehicles and additives.

To achieve a medium to dark golden bronze color, the preparation contains the following ingredients:
(a) the mixture of octyl salicylate, octyl methoxycinnamate and benzophenone-3 in a ratio of 1.0–2.0:0.8–2.5:0.8–2.0, where the amount of each individual UV filter is in the range of 3 to 7.5 percent by weight;
(b) DHA in a liposomal carrier system with a DHA content of 1.3 to 1.7 percent by weight, plus unencapsulated DHA in an amount of 2.7 to 3.8 percent by weight;
(c) an antioxidant mixture in an amount of 0.15 to 0.25 percent by weight;
(d) a moisturizer mixture with glycerol in an amount of 2.7 to 4 percent by weight;
and other cosmetic vehicles and additives.

To achieve a medium to dark rosy bronze color, the preparation contains the following ingredients:
(a) the mixture of octyl salicylate, octyl methoxycinnamate and benzophenone-3 in a ratio of 1.0–2.0:0.8–2.5:0.8–2.0, where the amount of each individual UV filter is in the range of 3 to 7.5 percent by weight;
(b) DHA in a liposomal carrier system with a DHA content of 1.2 to 1.6 percent by weight, plus additional unencapsulated DHA in an amount of 2.9 to 4.0 percent by weight;
(c) an antioxidant mixture in an amount of 0.05 to 0.07 percent by weight;
(d) a moisturizer mixture in an amount of 0.7 to 1.1 percent by weight;
plus other cosmetic vehicles and additives.

An especially preferred ratio for (a) is 1:2:1 for all three shades.

As explained above, in addition to the above-mentioned UV absorbers, which absorb UV-A and UV-B radiation, soluble melanin and butylmethoxydibenzoylmethane, which absorb UV-A radiation, may also be present.

The color shades achieved can be further enhanced or reduced by factors attributed to the skin of the individual user, so the desired skin color can be achieved essentially with the three basic colors described above.

It has surprisingly been found that the known negative effects of DHA do not occur at all or occur to such a limited extent in the combination according to this invention that they do not have any interfering effect. In particular, the known reactivity of DHA which leads to a disturbance in the equilibrium of a cosmetic preparation with a complicated formulation and thus leads to instability of the system, occurs here only to a greatly limited extent. A stable emulsion is obtained by working within the above limits of the amounts of individual ingredients. Encapsulation of DHA in phospholipid liposomes has proven advantageous, and it enhances the natural appearance of the skin after tanning.

Another surprising effect is that different and natural colors can be achieved with the given cosmetic preparation merely by varying the amount of these ingredients in the total preparation and adjusting the remaining ingredients accordingly, and stable emulsions can be obtained in the process.

The usual cosmetic vehicles, carriers and additives which may also be present in the preparation according to this invention include emulsifiers, various oil components (such as fats, oils, esters, silicone oil, etc.), other substances such as allantoin, thickeners, preservatives, perfume oils, chelating agents, active substances (such as allantoin), and water.

The invention is explained in greater detail by the examples given below, although they are not intended to restrict the scope of the invention in any way. The percentage amounts are always based on weight, unless otherwise indicated.

EXAMPLE 1

| Phase A | |
| --- | --- |
| glyceryl stearate/PEG-100 stearate | 7% |
| sorbitan stearate | 1% |
| palmitic acid | 2% |
| stearic acid | 2% |
| calendula oil | 1% |
| octyl palmitate | 12% |
| hydrogenated vegetable oil | 2% |
| cyclomethicone | 1% |
| dimethicone | 2% |
| mixture of vitamins C + E | 0.1% |
| octyl salicylate | 4% |
| benzophenone-3 | 7% |
| octyl methoxycinnamate | 4% |
| Phase B | |
| deionized water | 28.2% |
| glycerol | 5% |
| xanthan gum | 0.2% |
| Phase C | |
| laureth-7/polyacrylamide/C13-14 isoparaffin | 1% |
| Phase D | |
| preservative | 0.8% |
| Phase E | |
| deionized water | 5% |
| DHA | 3% |
| ethoxydiglycol | 7% |
| Phase F | |
| deionized water | 1% |
| aloe vera gel | 0.2% |
| Phase G | |
| perfume | 0.5% |
| Phase H | |
| DHA liposomes | 3% |

Eight phases were prepared separately and mixed together in succession, homogenizing well as needed. Phases A through D were incorporated at an elevated temperature (40° C. to 70° C.) and phases E through H were finally incorporated at ambient temperature while homogenizing.

This yielded a cream with moisturizing properties and a sunscreen factor SPF of 6 to 8. The tanning effect began approximately 40 minutes after applying the cream and yielded a medium to dark golden bronze. The tan lasted for approximately 12 days.

EXAMPLE 2

| Phase A | |
| --- | --- |
| steareth-2 and 21 | 4% |
| diethylene glycol + dioctanoate/diisononanoate | 2% |
| C12–15 alkyl benzoate | 4% |
| hydrogenated polyisobutene oil | 1% |
| calendula oil | 1% |
| babassu oil | 2% |
| PPG-15 stearyl ether | 2% |
| mixture of vitamins A + E | 0.1% |

| | |
|---|---|
| octyl salicylate | 4% |
| benzophenone-3 | 3% |
| octyl methoxycinnamate | 7% |
| Phase B | |
| deionized water | 32% |
| allantoin | 0.1% |
| Sodium salt of diethylenetetraacetic acid | 0.1% |
| xanthan gum | 0.2% |
| Phase C | |
| laureth-7/polyacrylamide/C13–14 isoparaffin | 4% |
| Phase D | |
| preservative | 0.5% |
| Phase E | |
| methyldibromoglutaronitrile/phenoxyethanol | 0.1% |
| cyclomethicone | 7% |
| Phase F | |
| deionized water | 1% |
| aloe vera gel | 0.2% |
| Phase G | |
| sodium hyaluronate | 0.2% |
| deionized water | 1% |
| Phase H | |
| deionized water | 5% |
| DHA | 3.5% |
| ethoxydiglycol | 7% |
| Phase I | |
| perfume | 0.5% |
| Phase J | |
| DHA liposomes | 7.5% |

The ten phases were prepared separately, then mixed together in order and homogenized. Phases A through D were incorporated at an elevated temperature (40° C. to 70° C.), and phases E through J were then incorporated at ambient temperature and homogenized.

This yielded a cream with moisturizing properties and a sunscreen factor SPF of 6 to 8. The tanning effect began approximately 30 to 40 minutes after application of the cream, yielding a medium to dark rosy bronze color. The tan lasted for approximately 10 to 14 days.

EXAMPLE 3

| | |
|---|---|
| Phase A | |
| glyceryl stearate/PEG-100 stearate | 7% |
| sorbitan stearate | 1% |
| palmitic acid | 2% |
| stearic acid | 1% |
| calendula oil | 1% |
| octyl palmitate | 5% |
| hydrogenated vegetable oil | 8% |
| cyclomethicone | 2% |
| dimethicone | 1% |
| mixture of vitamins A + E | 0.1% |
| octyl salicylate | 4% |
| benzophenone-3 | 3% |
| octyl methoxycinnamate | 7% |
| Phase B | |
| deionized water | 40.2% |
| glycerol | 4% |
| xanthan gum | 0.2% |
| Phase C | |
| laureth-7/polyacrylamide/C13–14 isoparaffin | 1% |
| Phase D | |
| preservative | 0.8% |
| Phase E | |
| deionized water | 5% |
| DHA | 2% |
| Phase F | |
| deionized water | 1% |
| aloe vera gel | 0.2% |
| Phase G | |
| perfume | 0.5% |
| Phase H | |
| DHA liposomes | 2% |

The procedure followed was the same as in Example 1.

This yielded a cream with moisturizing properties and a sunscreen factor SPF of 6 to 8. The tanning effect would begin approximately 30 to 40 minutes after applying the cream and produced a light glowing golden color. The tan lasted for approximately 10 to 14 days.

We claim:

1. A cosmetic self-tanning agent with a sunscreen effect based on dihydroxyacetone, comprising the following ingredients, based on the total weight of the emulsion:
   (a) 7 to 18.5 percent by weight of a mixture of the UV filters octyl salicylate, octyl methoxycinnamate and benzophenone-3 in a ratio of 1.0–2.0:0.8–2.5:0.8–2.0;
   (b) dihydroxyacetone (DHA) in a liposomal transport system consisting of DHA and phospholipids with a DHA content of 0.5 to 5 percent by weight, where the amount of liposomal solution is in the range of 1.5 to 25 percent by weight, plus also unencapsulated DHA in an amount of 1 to 4 percent by weight, each based on the total weight of the mixture;
   (c) an antioxidant selected from the group consisting of tocopherol, ascorbic acid, calendula extract and a mixture thereof, in an amount of 0.01 to 5.0 percent by weight of the total mixture;
   (d) a moisturizer selected from the group consisting of aloe vera, phospholipids, phospholipid mixtures, sodium hyaluronate, glycerol and mixtures thereof, in an amount of 0.1 to 16 percent by weight of the total mixture;
   and cosmetic vehicles and additives.

2. A cosmetic self-tanning agent according to claim 1, wherein the total amount of the UV filters (a) is in the range of 10 to 16 percent by weight.

3. A cosmetic self-tanning agent according to claim 1, wherein the amount of DHA (b) is in the range of 0.8 to 1.8 percent by weight, where the amount of the liposomal solution is in the range of 1.5 to 10.0 percent by weight.

4. A cosmetic self-tanning agent according to claim 1, wherein the amount of antioxidants (c) is in the range of 0.01 to 0.5 percent by weight.

5. A cosmetic self-tanning agent according to claim 1, wherein the amount of moisturizers (d) is in the range of 0.7 to 5 percent by weight.

6. A cosmetic self-tanning agent according to claim 1, wherein it contains the following ingredients to achieve a light golden color:
   (a) the mixture of octyl salicylate, octyl methoxycinnamate and benzophenone-3 in a ratio of 1.0–2.0:0.8–2.5:0.8–2.0, with the amount of each individual UV filter being in the range of 3 to 7.5 percent by weight;

(b) DHA in a liposomal carrier system with a DHA content of 0.5 to 1.0 percent by weight, plus unencapsulated DHA in an amount of 1.4 to 2.6 percent by weight;
(c) an antioxidant mixture of tocopherol, ascorbic acid and calendula extract in an amount of 0.15 to 0.25 percent by weight;
(d) a moisturizer mixture with glycerol in an amount of 2.5 to 4 percent by weight;

plus other cosmetic vehicles and additives.

7. A cosmetic self-tanning agent according to claim 1, wherein it contains the following ingredients to achieve a medium to dark bronze color:
(a) the mixture of octyl salicylate, octyl methoxycinnamate and benzophenone-3 in a ratio of 1.0–2.0:0.8–2.5:0.8–2.0, where the amount of each individual UV filter is in the range of 3 to 7.5 percent by weight;
(b) DHA in a liposomal carrier system with a DHA content of 1.3 to 1.7 percent by weight, plus unencapsulated DHA in an amount of 2.7 to 3.8 percent by weight;
(c) an antioxidant mixture of tocopherol, ascorbic acid and calendula extract in an amount of 0.15 to 0.25 percent by weight;
(d) a moisturizer mixture with glycerol in an amount of 2.7 to 4 percent by weight;

and other cosmetic vehicles and additives.

8. A cosmetic self-tanning agent according to claim 1, wherein it contains the following ingredients to achieve a medium to dark rosy bronze color:
(a) the mixture of octyl salicylate, octyl methoxycinnamate and benzophenone-3 in a ratio of 1.0–2.0:0.8–2.5:0.8–2.0, where the amount of each individual UV filter is in the range of 3 to 7.5 percent by weight;
(b) DHA in a liposomal carrier system with a DHA content of 1.2 to 1.6 percent by weight, plus additional unencapsulated DHA in an amount of 2.9 to 4.0 percent by weight;
(c) an antioxidant mixture of tocopherol, ascorbic acid and calendula extract in an amount of 0.02 to 0.04 percent by weight;
(d) a moisturizer mixture in an amount of 0.7 to 1.1 percent by weight;

plus other cosmetic vehicles and additives.

9. A cosmetic self-tanning agent according to claim 1 wherein the UV filters (a) comprise a mixture of octyl salicylate, octyl methoxycinnamate and benzophenone-3 in a ration of 1:2:1.

* * * * *